United States Patent [19]

Sherwin

[11] Patent Number: 4,851,219

[45] Date of Patent: Jul. 25, 1989

[54] METHOD FOR THE TREATMENT OF CHRONIC MYELOGENOUS LEUKEMIA

[75] Inventor: Stephen A. Sherwin, San Francisco, Calif.

[73] Assignee: Genentech, Inc., South San Francisco, Calif.

[21] Appl. No.: 932,434

[22] Filed: Nov. 18, 1986

[51] Int. Cl.$^4$ .............................................. A61K 45/02
[52] U.S. Cl. ................................. 424/85.5; 424/85.1; 424/85.6; 424/85.7
[58] Field of Search ....................... 424/85, 85.1, 85.2, 424/85.4, 85.6, 85.7; 530/351

[56] References Cited

U.S. PATENT DOCUMENTS 4,743,445  5/1988  Delwiche et al. ..................... 424/85

OTHER PUBLICATIONS

Chemical Abstracts, vol. 103, Abstract No. 140073w, 1985.
De Clereq et al., Cancer Letters, vol. 15, pp. 223–228, 1982.

Primary Examiner—Blondel Hazel
Attorney, Agent, or Firm—Walter H. Dreger

[57] ABSTRACT

Gamma interferon is employed in the treatment of chronic myelogenous leukemia. Patients treated in the benign stage exhibit partial and, in some cases, complete responses to gamma interferon. Successful results have also been obtained with some patients in the blast stage of the disease as well as patients who had been found to be refractory to treatment with alpha interferon.

9 Claims, No Drawings

METHOD FOR THE TREATMENT OF CHRONIC MYELOGENOUS LEUKEMIA

BACKGROUND OF THE INVENTION

This invention relates to the therapy of patients afflicted with chronic myelogenous leukemia (CML).

Chronic myelogenous leukemia (CML) is a chronic form of leukemia originating in a primitive myeloid stem cell in which the leukemic cells retain the capacity for differentiation and are able to perform the essential functions of normal hematopoietic cells that they replace in the marrow. The leukemic cells have a pronounced tendency to undergo further malignant transformation with loss of ability to differentiate in later stages of the disease. Although commonly included among other myeloproliferative disorders, CML is a distinct entity that is easily recognized because the leukemic cells have a distinctive cytogenetic abnormality, the Philadelphia ($Ph^1$) chromosome (also designated Ph+).

The etiology is unknown. The majority of patients with CML have no history of excessive exposure to ionizing radiation or chemical leukemogens, but the incidence increases greatly with exposure to high doses of radiation.

The incidence of CML in the United States and most Western countries is about 1.5 per 100,000 population per year and accounts for about 15 percent of all cases of leukemia.

Chronic myelogenous leukemia is a uniclonal neoplastic proliferation of hematopoietic stem cells. In about 90 percent of cases the leukemic cells have the unique Philadelphia ($Ph^1$) chromosome. The $Ph^1$ anomaly results from a reciprocal translocation of a portion of the long arm of chromosome 22 to another chromosome, usually the long arm of chromosome 9, although sometimes to another chromosome. Both deletion of the long arm of number 22 and translocation to another chromosome must be demonstrated by appropriate banding studies in order to confirm $Ph^1$ positivity.

The leukemic cells in chronic or benign phase CML have a striking propensity for further malignant transformation. After a variable duration of the chronic phase, averaging about three years, the disease enters an accelerated or, eventually, a blastic phase. Such malignant progression occurs in about 80 percent of patients and probably would eventually occur in all of them if they did not die of other complications of the disease or of unrelated causes. The rapidity with which the transition occurs depends on the degree of further transformation and on the comparative proliferative properties of the chronic and acute phase stem cells. In the accelerated phase the cells retain their capacity for partial differentiation, whereas in the blastic phase they are arrested at the blastic level of differentiation. The direction of differentiation in the accelerated phase is variable, as it is in the chronic phase. Transitional forms may occur between the chronic, accelerated, and blastic phases.

The most consistent laboratory abnormality at diagnosis of CML is leukocytosis. The white blood cell count (WBC) may range from a minimal elevation to over a million leukocytes per cubic millimeter. Increased numbers of eosinophils and/or basophils are often present, and sometimes monocytosis is seen. Increased megakaryocytes are often found in the marrow. The myeloid:erythroid ratio in the marrow is usually greatly elevated. The percentage of blasts in the marrow and blood is usually less than 3 percent in the chronic phase at diagnosis and less than 1 percent after the WBC has been reduced by treatment; a persistant elevation of greater than 10 percent usually indicates impending transformation. About half of patients present with some degree of thrombocytosis at diagnosis; thrombocytopenia is much less frequent. Extreme degrees of thrombocytopenia or thrombocytosis may develop as the disease progresses. In some patients, cyclic fluctuations of the leukocytes and platelets have been observed that are unrelated to treatment.

Transition from the chronic phase to the accelerated or blastic phase may occur gradually over a year or longer or abruptly ("blast crisis"). There are no standardized criteria for distinguishing between the accelerated and blastic phases, but most authorities use a persistant elevation of greater than 20 or 30 percent blasts in the blood and/or marrow or of blasts plus promyelocytes of 30 percent in blood or 50 percent in marrow to define the blastic phase.

Asymptomatic patients in the chronic phase in whom the WBC is below 50,000 per cubic millimeter can be observed without treatment until the disease progresses and symptoms develop. When clinical manifestations appear they can usually be controlled with cytotoxic drugs such as busulfan, or by splenic irradiation or splenectomy but unlike in acute leukemia, true remissions are very rare and the marrow remains largely populated with leukemic cells containing the $Ph^1$ marker. Allogenic transplants have been employed successfully when compatible marrow has been available.

When CML enters an accelerated phase it becomes increasingly refractory to therapy that was previously effective. Increasing doses of busulfan or hydroxyurea are required to control the WBC and spleen size and, in some cases, progressive thrombocytosis. In some cases, severe anemia and/or thrombocytopenia develop, either because of the disease or as a result of drug toxicity.

Alpha interferon has been employed in clinical trials in an effort to treat GML (M. Talpaz et al., "Blood" 62:689–692 [1983]), and has received approval from the Food and Drug Administration for the treatment of hairy cell leukemia.

Gamma interferon, a structurally distinct molecule known to have a receptor site distinct from that of alpha interferon (M. Aguet et al., "Virology" 117:541 [1982]), has been proposed for use in treating malignancies. For example, see R. Silver et al., "The American Journal of Medicine" 80:1137 (June, 1986). A preliminary report of the results described herein was published by R. Kurzrock et al., "Blood" 66 (Sup. 1) 291a (Nov. 1985).

Gamma interferon is known to exert effects on leukemic cell growth and differentiation in in vitro cell culture (T. Hosoi et al., "Exp. Hematol." 13:597 [1985]; W. Rigby et al., "Blood" 65:858 [April 1985]; and S. Buessow et al., "J. Biol. Res. Mod." 3:653 [1984]).

Accordingly, methods are needed for the treatment and control of CML which are ore effective and which are not characterized by the severe side effects prevalent with conventional therapies for this disease.

SUMMARY OF THE INVENTION

Surprisingly, it was found that patients who had relapsed or become refractory to treatment of CML during the aforementioned clinical trial using alpha interferon nonetheless responded clinically to treatment using a gamma inteferon dosing regimen. Accordingly, the object herein is accomplished by the administration to a patient having CML of a therapeutically effective dose of gamma interferon.

DETAILED DESCRIPTION OF THE INVENTION

Gamma interferon is a well characterized lymphokine which may be obtained in homogeneous dosage forms from recombinant or native sources. Any source of gamma interferon is acceptable so long as the interferon is in a physiologically acceptable vehicle or excipient and it is species compatible, e.g. human gamma interferon should be used in the therapy of humans. Amino acid sequence variants of gamma inteferon are useful so long as they exhibit the biological activity of gamma interferon.

Typically gamma interferon is administered intravenously or intramuscularly after sterile reconstitution from vials containing homogeneous desCysTyrCys human gamma interferon. The interferon is reconstituted in sterile water for injection or sterile 5% w/vol dextrose, although other conventional administration vehicles can be employed, e.g., sustained release formulations, albumin, isotonic saline and the like.

The dosage to be administered will depend upon the stage of progression of CML in the patient in question (benign, accelerated or blastic phase), the general clinical condition of the patient, the concomitant use of chemotherapeutic agents and other factors known to the clinician. In general, a dose of about 0.25 mg/m2/day by single intramuscular injection is suitable, although lower doses may be efficacious in some circumstances. The maximum tolerated dose in these patients, i.e., the dose at which typical gamma interferon side effects (chills, fever and the like) began to appear, was about 0.5 mg/m2/day. Higher doses are within the scope hereof should the clinical advantage outweight these relatively benign side effects.

Responses such as the one reported in Example 1 below have generally occurred within 2 weeks of the onset of treatment.

Gamma interferon optionally is used with other antineoplastic agents such as alpha or beta interferon, tumor necrosis factors such as TNF-$\alpha$ or TNF-$\beta$, or conventional alkylating agents such as busulfan. Synergistic reponses are noted in some cases. Accordingly, it is desirable for the clinician to combine gamma interferon with other agents on a empirical basis in order to identify particularly active combinations.

Gamma interferon preferably is used in patients who are lodged in a pre-blastic phase of CML. The objective here is to prevent the leukemia from transforming into the most pathological and generally terminal phase of this disease, the blastic phase. Gamma interferon has been found not only to suppress the progression of CML into the blast phase but has also apparently induced clinical regressions in some cases—notwithstanding the continued presence of the Philadelphia chromosome in the lymphatic cells of such patients. Furthermore, gamma interferon has been found to be effective in patients who were or became nonresponsive to alpha interferon.

The following examples are intended to illustrate the invention but are not to be construed as limiting same.

EXAMPLE 1

Case Report

A 45 year-old female with benign phase chronic myelogenous leukemia was begun on rIFN-$\gamma$ two years after the time of her initial diagnosis. She had been previously treated with interferon-alpha with good clinical response; however, she had subsequently developed neutralizing antibody to interferon-alpha and concomitant resistance to its effects. After starting daily intramuscular rIFN-$\gamma$ therapy (0.25 mg/m$^2$/day), she manifested evidence of an ongoing hematological response with reduction of both WBC/mm$^3$ from 98,000 (pretherapy) to 7,900 (at 6 months) and platelets/mm$^3$ from 393,000 (pretherapy) to 224,000 (at 6 months). Bone marrow cytogenetics (percent Ph+) have not changed from a pretherapy level of 100 percent.

EXAMPLE 2

Daily rIFN-$\gamma$ in the Treatment of Chronic Myelogenous Leukemia

The method of Example 1 was essentially repeated with a number of additional patients. The results achieved with the patient population enrolled in the CML study are reported in the following Table.

TABLE 1

| | | | 6 of 14 evaluable chronic phase patients with response | | | |
|---|---|---|---|---|---|---|
| Patient | Time Since Diagnosis | Previous Therapy | Bone Marrow and Cytogenetics (before/After) | WBC/mm$^3$ Before/After | Platelets/mm$^3$ Before/After | Duration |
| N.C. | 2 yrs. | $\alpha$ interferon (developed antibodies and resistance) | 100% Ph+/ no change | 98,000/7,900 | 393,000/224,000 | 6+ mos. |
| O.E. | 2½ yrs. | $\alpha$ interferon myleran | 100% Ph+/ no change | 108,000/40,000 | 890,000/500-700,000 | 7+ mos. |
| J.R. | 2 mos. | none | Ph+/50% improvement | 53,000/3,400 (lymphs + monocytes 10% — >40%) | 874,000/425,000 | 10+ mos. |
| R.L. | 4 yrs. | myleran hydrea | 100% Ph+ 7.4% blast 7.4% progran/Blasts 0.6% progran 0.6% | 62,000/17,500 | 533,000/231,000 | 15+ mos. |
| K.F. | 2½ yrs. | myleran $\alpha$ interferon | 100% Ph+/ no change | 136,000/12,000 | 96,000/70,000 | 4+ mos. |
| C.J. | 3 yrs. | myleran | 100% Ph+/ 80% Ph+ 50% diploid | 39,000/6,100 | 209,000/215,000 | 9+ mos. |

I claim:

1. A method for the treatment of chronic myelogenous leukemia comprising administering to a patient with chronic myelogenous leukemia a therapeutically effective dose of gamma interferon.

2. The method of claim 1 wherein the dosage is about 0.25 mg/m2/day.

3. The method of claim 2 wherein the gamma interferon is administered intramuscularly.

4. The method of claim 1 wherein an additional agent is administered which is selected from the group consisting of alpha interferon, beta interferon, tumor necrosis-factor-$\alpha$, tumor necrosis-factor-$\beta$ and chemotherapeutic agents.

5. The method of claim 4 wherein the chemotherapeutic agent is an alkylating agent.

6. The method of claim 5 wherein the agent is busulfan.

7. The method of claim 1 wherein the gamma interferon is administered continuously by infusion.

8. The method of claim 1 wherein the patient is in a pre-blastic phase.

9. The method of claim 1 wherein the patient was previously nonresponsive to alpha interferon when administered alone.

* * * * *